United States Patent [19]

Deschler et al.

[11] Patent Number: 4,837,322
[45] Date of Patent: Jun. 6, 1989

[54] MIXTURES OF SULFUROUS TRIAZINE COMPOUNDS

[75] Inventors: Ulrich Deschler, Hanau; Georg Hellwig, Gründau; Rudolf Michel, Freigericht; Peter Kleinschmit, Hanau; Siegfried Wolff, Bornheim, all of Fed. Rep. of Germany

[73] Assignee: Degussa Aktiengesellschaft, Frankfurt am Main, Fed. Rep. of Germany

[21] Appl. No.: 89,895

[22] Filed: Aug. 27, 1987

[30] Foreign Application Priority Data

Sep. 4, 1986 [DE] Fed. Rep. of Germany ....... 3630055

[51] Int. Cl.⁴ .................. C07D 403/12; C07D 403/14
[52] U.S. Cl. ................................. 544/209; 544/113; 544/60; 544/58.5; 540/598
[58] Field of Search ................. 544/198, 113, 60, 209, 544/58.5; 540/598

[56] References Cited

FOREIGN PATENT DOCUMENTS 3438290 4/1986 Fed. Rep. of Germany .

*Primary Examiner*—John M. Ford
*Attorney, Agent, or Firm*—Cushman, Darby & Cushman

[57] ABSTRACT

Mixtures of sulfurous triazine compounds and methods of preparing these compounds with the general formula

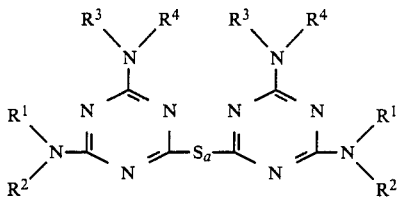

in which
$R^1$, $R^2 = H, R^2 =$ benzyl,
$R^2$, $R^3$, $R^4 = C_1-C_8$-alkyl, allyl, $C_3-C_8$ cycloalkyl, the latter unsubstituted or substituted with 1-3 methyl groups, 2-hydroxyethyl, 3-hydroxypropyl, 2-hydroxypropyl or
$R^3$ and $R^4$ (together): $C_4-C_6$-alkylene, $-(CH_2-CHX)_2Y$ with
$X = H, CH_3, Y = O, S$,
$S_a$: Polysulfide chain with 2-10 S atoms (i.e. $2 \leq a \leq 10$), in which the individual polysulfides are present in such concentrations that the statistical average value of "a" is a whole or fractional numerical value in the range from 2 to 5., characterized in that a triazine compound of the general formula

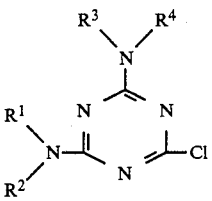

in which $R^1$, $R^2$, $R^3$, $R^4$ have the meanings indicated above is reacted with an ammonium polysulfide or alkali polysulfide and dissolved in a protic polar solvent, especially water, at a temperature of 80° to 140° C.

4 Claims, No Drawings

MIXTURES OF SULFUROUS TRIAZINE COMPOUNDS

The invention is relates to mixtures of sulfurous triazine compounds and methods of their preparation.

BACKGROUND OF THE INVENTION

DE-PS No. 1,699,954 discloses bis-(2-ethylamino-4-diethylamino-s-triazine-6-yl) disulfide. This compound can be prepared, for example, from the corresponding monomercaptotriazine by oxidation with iodine or hydrogen peroxide. The compound obtained in this manner is used as a vulcanization accelerator in rubber mixtures.

The corresponding tetrasulfide is described in DE-OS No. 34 38 290.

The latter compound is produced by the reaction of a mercaptotriazine with $S_2Cl_2$ and is used successfully in vulcanizable mixtures as a vulcanizing agent or as a vulcanization accelerator.

The same action is developed by such mixtures of bistriazinyl polysulfides in which the two triazine rings are not connected by a defined $S_4$ bridge but rather by a polysulfide chain with a statistical average length of four sulfur atoms (German patent application P No. 36 10 794).

SUMMARY OF THE INVENTION

The present invention is concerned with a method of producing mixtures of sulfurous triazine compounds of the general formula

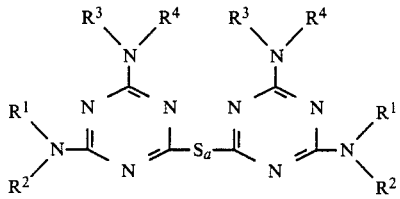

in which:

$R^1$ and $R^2$ may be hydrogen, $R^2$ may be benzyl, $R^2$, $R^3$ and $R^4$ may be $C_1$–$C_8$-alkyl, allyl, $C_3$–$C_8$ cycloalkyl, the latter being unsubstituted or substituted with 1-3 methyl groups, 2-hydroxyethyl, 3-hydroxypropyl or 2-hydroxypropyl or $R^3$ and $R^4$ (together) may be $C_4$–$C_6$-alkylene, —(CH$_2$—CHX)$_2$Y where X is hydrogen or $CH_3$ and Y is O or S, $S_{\bar{a}}$ is a polysulfide chain with 2-10 sulfur atoms (i.e. $2 \leq a \leq 10$), in which the individual polysulfides are present in such proportions that the statistical average value of "a" is a whole or fractional numerical value in the range from 2 to 5.

The method of the invention comprises reacting a triazine compound of the general formula

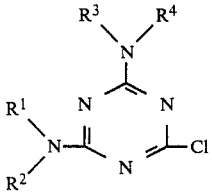

in which $R^1$, $R^2$, $R^3$, $R^4$ have the meanings indicated above, with a compound of the formula $$Me_2S_{\bar{a}} \qquad \text{III}$$

dissolved in a protic polar solvent, especially water or its mixtures with water, in which Me signifies the ammonium cation or an alkali cation, preferably Na$^+$ or K$^+$ and $\bar{a}$ corresponds to the statistical average with $2 \leq a \leq 5$ in a molar ratio of 2:1 to 2:1.1 at a temperature of 80° to 140° C. and the product is separated from the accumulating reaction mixture by known procedures.

The reaction is preferably allowed to occur at the reflux temperature which develops; water forms the main component of the solvent, especially at 95° to 100° C. However, it is also possible to perform the reaction at higher temperatures in a pressure vessel.

In a preferred embodiment, the molten compound of the Formula II is added dropwise into a strongly alkaline aqueous solution of $Me_2S_{\bar{a}}$ which is heated to 100° C.

The pH decreases in the aqueous reaction mixture during the reaction. Therefore, in a preferred embodiment, an aqueous alkaline solution, e.g. sodium hydroxide solution or sodium bicarbonate solution, is continuously added during the reaction, especially if the solvent is predominantly or entirely water, so that the pH does not decrease below 9.0 to 7.5, especially to 8.5.

The $Me_2S_{\bar{a}}$ added is statistically composed as concerns the length of the polysulfide chain. Therefore, the stoichiometric factor of 4 in $Na_2S_4$, for example, only implies that the $S_a^2$ dianions with $2 \leq a \leq 10$ present in the mixture are present in such proportions that the following relationship is fulfilled:

$$\frac{\Sigma n_a \cdot a}{n} = 4 = \bar{a}$$

in which
n = total number of dianions present
$n_a$ = number of dianions of chain length a present
$\bar{a}$ = statistical average.

Since all dianions present in $Me_2S_{\bar{a}}$ exhibit nucleophilic properties in chemical reactions, it is possible to control the statistical composition of the polysulfide chain lengths by the selection of the raw material.

The reaction is completed after at most 3 hours at 100° C. in an aqueous medium. As a precaution, the reaction mixture can also be heated under a reflux for a longer time.

Subsequently, the sulfurous triazine derivative which forms a lower phase is allowed to run off as a hot liquid, and it is then cooled and residual moisture is removed by drying, e.g. in a vacuum.

The product may be converted into the finely divided particulate form necessary for use in rubber mixtures by conventional procedures, e.g. by grinding.

If analysis indicates free sulfur in the final product, a purification can be performed, e.g. by dissolving the crude product in hot ethanol.

Thereafter, impurities such as sulfur or NaCl can be separated out by filtration.

The process can be modified by introducing the $Me_2S_{\bar{a}}$ in a solution in ethanol, for example, or by using n-propanol or glycol as a solvent alone, or in mixtures of those alcohols with water.

The triazine derivative according to Formula II is then added in powder form or, preferably, it is first dissolved or suspended in the corresponding alcohol or put up in another variant and then mixed with the $Me_2S_{\bar{a}}$ solution. In order to separate the product, the reaction mixture can then be compounded with water, for example, and filtered. The insoluble filter residue is then dried and ground.

The invention also provides mixtures of sulfurous triazine compounds of the general formula

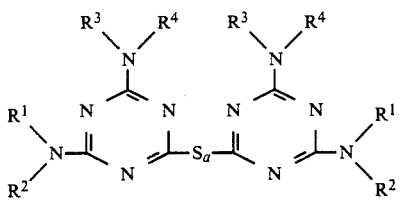

in which:
$R^1$ and $R^2$ may be hydrogen, $R^2$ may be benzyl,
$R^2$, $R^3$ and $R^4$ may be $C_{1-8}$- alkyl, allyl, $C_3$–$C_8$ cycloalkyl, the latter being unsubstituted or substituted with 1–3 methyl groups, 2-hydroxyethyl, 3-hydroxypropyl or 2-hydroxypropyl or $R^3$ and $R^4$ (together) may be $C_4$–$C_6$-alkylene, —($CH_2$—$CHX$)$_2$ Y in which
X is H or $CH_3$ and Y is O or S,
$S_{\bar{a}}$ is a polysulfide chain with 2–10 sulfur atoms (i.e. $2 \leq a \leq 10$), in which the individual polysulfides are present in such proportions that the statistical average value of "a" is a whole or fractional numerical value in the range from 2 to 5, with the exception of 4.

DETAILED DESCRIPTION OF PREFERRED EMBODIMENTS

When used as vulcanizing agents or vulcanization accelerators in rubber mixtures the compounds of the present invention produce vulcanizates having outstanding properties.

The following products are cited as examples of preferred mixtures which can be produced in accordance with the method of the invention:

A  bis-(2-ethylamino-4-di-isopropylamino-s-triazin-6-yl)-oligosulfide
B  bis-(2-n-butylamino-4-diethylamino-s-triazin-6-yl)-oligo-sulfide
C  bis-(2-isopropylamino-4-di-isopropylamino-s-triazin-6-yl)-oligosulfide
D  bis-(2-ethylamino-4-di-isobutylamino-s-triazin-6-yl)-oligosulfide
E  bis-(2-ethylamino-4-di-n-propylamino-s-triazin-6-yl)-oligosulfide
F  bis-(2-n-propylamino-4-diethylamino-s-triazin-6-yl)-oligosulfide
G  bis-(2-n-propylamino-4-di-n-propylamino-s-triazin-6-yl)-oligosulfide
H  bis-(2-n-butylamino-4-di-n-propylamino-s-triazin-6-yl)-oligosulfide
I  bis-(2-ethylamino-4-di-n-butylamino-s-triazin-6-yl)-oligosulfide
K  bis-(2-cyclohexylamino-4-diethylamino-s-triazin-6-yl)-oligosulfide
L  bis-(2-ethylamino-4-diethylamino-s-triazin-6-yl)-oligosulfide
M  bis-(2-amino-4-diethylamino-s-triazin-6-yl)-oligosulfide The oligosulfides are mixtures of compounds in which the individual polysulfides have an S chain length in the range $2 \leq a \leq 10$ and the proportions of the individual compounds are such that the statistical average of the S chain lengths is a whole or fractional numerical values in the range from 2 to 5 ($2 \leq a^- \leq 5$).

The invention is illustrated by the following examples:

EXAMPLE 1

229.7 g (1.0 mole) 2-ethylamino-4-diethylamino-6-chlorotriazine, 95.8 g (0.55 mole) of a disodium polysulfide mixture having a statistical composition $Na_2S_4$ (prepared in accordance with the procedure disclosed in DE-OS No. 34 36 698) as well as 1000 ml $H_2O$ are placed successively in a 2 liter three-neck flask which is equipped with a KPG agitator, reflux condenser and pH electrode, and this reaction mixture is heated to reflux temperature over a period of 30 minutes. The pH is initially 10.7, but it gradually drops and reaches a value of pH=8.5 after 2 hours reflux time. During this time, the color of the reaction medium changes from deep orange-brown to yellow. The mixture is agitated one hour further, under reflux, while the pH is held a $\geq 8.5$ by adding an aqueous NaOH solution (20%) (consumption: 0.1 mole NaOH). After the KPG agitator is turned off, a 2-phase system develops, in which the heavier portion consists essentially of the product mixture. This layer is separated via a bottom outlet valve from the aqueous phase and solidifies to a yellowish brown amber-like solid (solidification point approx. 90° C.). The approximately 5% of moisture residues contained therein are removed by vacuum treatment (15 torr) at 95° C. for 16 hours until a residual moisture of $\leq 0.5\%$. The solid obtained in this manner can be comminuted in a mortar to a powder which can trickle at room temperature. This powder can dissolve in ethanol to form a clear solution, that is, it contains no significant amounts of elementary sulfur or of NaCl.

Yield: 246.5 g corresponding to 95.4% of theory, bright yellow powder.

Elementary analysis: $C_{18}H_{32}N_{10}S_4$ (516.76)

|  | C | H | N | S | Cl |
|---|---|---|---|---|---|
| calculated: | 41.84 | 6.24 | 27.10 | 24.82 | 0 |
| found: | 41.07 | 6.24 | 26.80 | 24.80 | 0.1 |

HPLC analysis (according to a known method, K. O. Hiller et al.; Zeitschrift Analyt. Chem. Vol 280 (1976) p. 293:

| Compound (*) | rel. area % (**) |
|---|---|
| R—$S_2$—R | 48.5 |
| R—$S_3$—R | 12.6 |
| R—$S_4$—R | 18.8 |
| R—$S_5$—R | 8.8 |
| R—$S_6$—R | 6.7 |
| R—$S_7$—R | 3.1 |
| R—$S_8$—R | 1.5 |

(*) R = 2-ethylamino-4-diethylamino-6-triazinyl
(**) neglecting the peak areas caused by the mobile solvent, standardization at 100 area %

EXAMPLE 2

25.5 g (0.130) mole diammonium pentasulfide (preparation according to J. S. Thomas et al., J. Chem. Soc. 1923, pp. 1726 ff.) are dissolved in 300 ml water in a standard apparatus analogous to the one described in Example 1. 57.4 g (0.25 mole) liquified 2-ethylamino-4-diethylamino-6-chlorotriazine (melting point: 98° C.) was added to the reddish brown ammonium polysulfide solution at reflux temperature within 30 min. from a heated dropping funnel while the mixture was agitated. The reaction solution is agitated for another 90 min. under reflux, while the initially measured pH of 11.7 drops slowly to 8.0. The pH is maintained for the following 60 min. at 9.0 by adding an aqueous NaOH solution (consumption: 0.04 mole NaOH). As was described in Example 1, the preparation mixture is isolated through a bottom outlet valve, dried and powdered. 66.3 g of a yellowish powder is obtained which is not completely soluble in hot ethanol. After treatment in a Soxhlet extractor with 150 ml ethanol, 2.6 g of a yellow powder with a sulfur content of 98.6% remains. The preparation is isolated from the extract by means of drawing off the solvent.

Yield: 63.2 g corresponding to 92.1% of theory (in relation to a statistically composed pentasulfane), bright yellow powder Elementary analysis: $C_{18}H_{32}N_{10}S_{4.5}$ (532.79)

|  | C | H | N | S | Cl |
|---|---|---|---|---|---|
| calculated: | 40.58 | 6.05 | 26.29 | 27.08 | 0 |
| found: | 41.12 | 6.43 | 27.12 | 26.61 | 0.2 |

HPLC-analysis

| Association | Rel. area % |
|---|---|
| $R-S_2-R$ | 9.0 |
| $R-S_3-R$ | 29.8 |
| $R-S_4-R$ | 37.8 |
| $R-S_5-R$ | 12.4 |
| $R-S_6-R$ | 6.5 |
| $R-S_7-R$ | 3.1 |
| $R-S_8-R$ | 1.4 |

71.8 g of a bright yellow solid corresponding to 96.3% of m. are isolated which gave the following analytical data:
$C_{26}H_{48}N_{10}S_3$ (596.93):

|  | C | H | N | S | Cl |
|---|---|---|---|---|---|
| calculated: | 52.31 | 8.11 | 23.46 | 16.11 | 0 |
| found: | 52.67 | 8.62 | 23.83 | 15.89 | 0.15 |

The HPLC diagram contains signals for bistriazinyl disulfane (45.7% area), the corresponding tri- (39.1%), tetra- (12.8%) and pentasulfane (2.4%).

EXAMPLE 4

The method described in Example 1 is performed with the following materials:
- 71 g (0.25 mole) 2-cyclohexylamino-4-diethylamino-6-chlorotriazine;
- 13.8 g (0.13 mole) disodium disulfide (preparation cf. Brauer, vol. 1, p. 374);
- 300 ml water.

54.3 g of bright yellow solid corresponding to 87.4% of m. are isolated with the following analytical data: $C_{26}H_{44}N_{10}S_2$ (560.84):

|  | C | H | N | S | Cl |
|---|---|---|---|---|---|
| calculated: | 55.68 | 7.91 | 24.97 | 11.43 | 0 |
| found: | 56.21 | 7.98 | 25.31 | 10.73 | 0.4 |

The HPLC diagram contains signals for bistriazinyl disulfane (89.1 area %) adjacent to signals for the corresponding tri-(9.7%) and tetrasulfane (1.2%).

EXAMPLES 5-9

The method described in Example 2 (addition of 2-ethylamino-4-diethylamino-6-chlorotriazine in liquid form) was performed using disodium polysulfides (preparation from the elements according to DE-OS No. 34 36 698) in various solvents. Reaction and preparation data are listed in Tables 1 and 2. For product preparation, the reaction mixture was compounded with water at 95° C. until a distinct phase separation of the molten bistriazinyl polysulfides from the solvents had occurred.

TABLE 1

Reaction Data for Examples 5-9

| Example No. | Solvent | a in $Na_2S_a$ | Proportions Chlorotriazine (*) (mol) | $Na_2S_a$ (mol) | Solvent (ml) | Reaction Conditions Time (hours) | Temperature (°C.) |
|---|---|---|---|---|---|---|---|
| 5 | Ethanol | 4.0 | 0.5 | 0.25 | 200 | 5.0 | 120 (**) |
| 6 | Glycol | 4.5 | 0.25 | 0.13 | 150 | 6.5 | 100-140 |
| 7 | n-propanol + water | 4.0 | 0.25 | 0.13 | 150 + 25 | 5.5 | 93-98 |
| 8 | glycol | 3.5 | 0.25 | 0.13 | 150 | 6.0 | 100-140 |
| 9 | glycol | 5.0 | 0.25 | 0.13 | 200 | 4.5 | 100-140 |

(*) denotes 2-ethylamino-4-diethylamino-6-chlorotriazine
(**) autoclave test

EXAMPLE 3

The method described in example 1 is performed with the following starting materials:
- 71.4 g (0.25 mole) 2-ethylamino-4-di-n-butylamino-6-chlorotriazine;
- 22.7 g dipotassium trisulfide (preparation cf. Brauer, vol. 1, p. 375);
- 250 ml water.

TABLE 2

Product Data for Examples 5-9

| Example No. | Raw Yield % | Amount of $S_8$ (*) | Elemental Analysis (**) (%) C | H | N | S | Cl |
|---|---|---|---|---|---|---|---|
| 5 | 72.5 | 6.2 | 44.93 | 7.00 | 29.07 | 19.70 | 0.1 |
| 6 | 83.4 | — | 39.74 | 6.00 | 25.04 | 26.00 | 0.3 |
| 7 | 90.5 | — | 41.68 | 6.18 | 28.29 | 24.10 | 0.2 |
| 8 | 79.3 | — | 44.21 | 6.41 | 27.82 | 23.10 | 0.2 |

TABLE 2-continued

| | Product Data for Examples 5-9 | | | | | | |
|---|---|---|---|---|---|---|---|
| 9 | 74.7 | 3.8 | 40.91 | 6.21 | 27.07 | 26.70 | 0.3 |

(*) determined by extraction with ethanol
(**) Calculated for

| | C | H | N | S |
|---|---|---|---|---|
| a = 3.0 | 44.60 | 6.65 | 28.90 | 19.84 |
| a = 3.5 | 43.18 | 6.64 | 27.97 | 22.41 |
| a = 4.0 | 41.84 | 6.24 | 27.10 | 24.82 |
| a = 4.5 | 40.58 | 6.05 | 26.29 | 27.08 |
| a = 5.0 | 39.39 | 5.88 | 25.82 | 29.21 |

What is claimed is:

1. A method of preparing mixtures of sulfurous triazine compounds of the formula

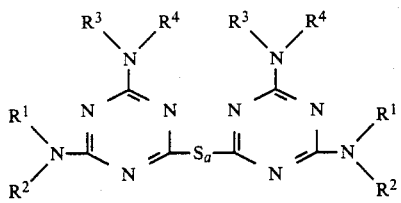

in which:
   $R^1$ is hydrogen, $R^2$ is selected from the group consisting of hydrogen, benzyl, $C_1$–$C_8$-alkyl, allyl, $C_3$–$C_8$ cycloalkyl, the latter unsubstituted or substituted with 1–3 methyl groups, 2-hydroxethyl 2-hydroxypropyl and 3-hydroxypropyl,
   $R^3$ and $R^4$ are $C_1$–$C_8$- alkyl, allyl, $C_3$–$C_8$ cycloalkyl, the latter unsubstituted or substituted with 1–3 methyl groups, 2-hydroxethyl, 3-hydroxypropyl or 2-hydroxypropyl or $R^3$ and $R^4$ (together) may be $C_4$–$C_6$-alkylene or —$(CH_2X)_2Y$ where
   X is H or $CH_3$ and Y is O or S
   $S_a$ is a polysulfide chain with 2–10 S atoms (i.e. $2 \leq a \leq 10$), in which the individual polysulfides are present in such proportions that the statistical average value of "a" is a whole or fractional numerical value in the range from 2 to 5 which method comprises reacting a triazine compound of the formula

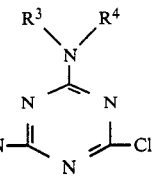

in which $R^1$, $R^2$, $R^3$, $R^4$ have the meanings indicated above, with a compound of the formula $$Me_2S_a \qquad III$$

dissolved in a protic polar solvent in which Me signifies the ammonium cation or an alkali cation, and $a$ corresponds to the statistical average with $2 \leq a \leq 5$ in a molar ratio of 2:1 to 2:1.1 at temperature of 80° to 140° C. and separating the product from the accumlating reaction mixture.

2. A method as set forth in claim 1 in which the protic polar solvent is water.

3. A method as set forth in claim 1 in which the compound of Formula I is added in molten form into the aqueous solution of the compound of Formula II heated to 95° to 100° C. and an aqueous alkaline solution is added during the reaction which occurs at this temperature in such a manner that the pH of the reaction mixture does not drop below 7.5 to 9.0.

4. A method according to claim 1 in which the compounds of Formulas I and II are placed in the solvent and are then heated to the reaction temperature.

* * * * *